United States Patent [19]

Narayanan et al.

[11] Patent Number: 5,229,354
[45] Date of Patent: Jul. 20, 1993

[54] LEACHING INHIBITION OF CROP TREATING CHEMICALS WITH NITROGEN CONTAINING POLYMERS

[75] Inventors: Kolazi S. Narayanan, Palisades Park; Ratan K. Chaudhuri, Butler, both of N.J.

[73] Assignee: ISP Investments Inc., Wilmington, Del.

[21] Appl. No.: 843,024

[22] Filed: Feb. 28, 1992

[51] Int. Cl.$^5$ .............. A01N 25/10; A01N 25/22; A01N 25/24; A01N 43/70
[52] U.S. Cl. .............. 504/113; 504/232; 504/324; 504/342; 71/DIG. 1
[58] Field of Search .......... 71/93, 115, 118, DIG. 1; 504/113

[56] References Cited

U.S. PATENT DOCUMENTS

| | | | |
|---|---|---|---|
| 3,886,125 | 5/1975 | Chromecek | 71/DIG. 1 |
| 4,129,435 | 12/1978 | Takematsu et al. | 71/93 |
| 5,022,917 | 6/1991 | Allan | 71/DIG. 1 |

Primary Examiner—Glennon H. Hollrah
Assistant Examiner—S. Mark Clardy
Attorney, Agent, or Firm—Marilyn J. Maue; Joshua J. Ward

[57] ABSTRACT

This invention relates to inhibiting leaching of crop treating chemicals into the ground water, aqua-system and surrounding soil of the treatment site by contacting the plant or plant site with an effective leach inhibiting, plant tolerating amount of a nitrogen-containing copolymer having pendant nitrogenous groups which contains between about 40 and about 98 wt. % of monomer unit A defined by the formula

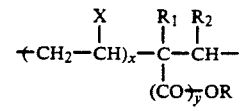

A.

and 2 to 40 wt. % of comonomer unit B

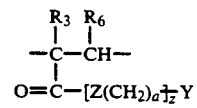

B.

wherein
X is hydrogen, a $C_1$ to $C_{22}$ radical of the group alkyl, alkoxy, aryl, alkaryl, aryloxy and alkaryloxy;
$R_2$ is hydrogen or $-(CO)_{y'}OR'$;
R, $R_1$, $R_3$ and R' are each selected from the group of hydrogen and lower alkyl;
$R_6$ is hydrogen or

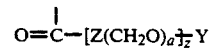

x, y, y' and z each have a value of 0 or 1;
a has a value of from 2 to 4;
Z is —O— or —NH—
Y is an optionally quaternized group of

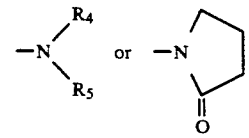

and
$R_4$ and $R_5$ are hydrogen or lower alkyl except that at least one of $R_4$ and $R_5$ is lower alkyl.

19 Claims, No Drawings

LEACHING INHIBITION OF CROP TREATING CHEMICALS WITH NITROGEN CONTAINING POLYMERS

In one aspect, this invention relates to a polymeric material which is readily incorporated into an agrichemical formulation in order to inhibit leaching of the active agrichemical into the ground water and surrounding area of treatment. In another aspect the invention relates to a composition for more effective use and reduced amounts of an active agrichemical.

BACKGROUND OF THE INVENTION

Agrichemical contamination is a growing concern since more than 12 different pesticides have been found in the ground water in at least 25 states in this country alone. Studies have shown that pesticide residues in ground water are increasing and are particularly severe where agronomic and horticultural crops are grown in permeable sandy soils or in locations which receive heavy rainfall. Among the chemicals which are particularly troublesome are herbicides such as bromacil, atrazine, metribuzin, dicamba and metolachlor, nematicides such as aldicarb, fungicides such as triforine, penconazole and insecticides such as bendiocarb, diazinone, chloropyrophos and ethion, which have been found in drinking water. Hence, there is an acute need to restrict the downward movement of pesticides, herbicides and other organic pollutants in the soil without reducing their agricultural efficacy.

Control of agrichemical leaching is a complex art which depends on many factors including rainfall, soil acidity and type, as well as plant tolerance. Various solutions to the problem have been proposed including controlled release formulations and encapsulated suspensions of the harmful active chemical. Surfactants have been employed for restricting the downward movement of urea herbicides such as diuron, linuron and monuron (see Weeds, by D. E. Bayer, Vol. 15, pages 249-252, 1967). The mobility of metribuzin in the soil has been reduced by the use of polyvinyl alcohol polymers, as discussed by C. L. McCormick and M. M. Fooladi, (1980) (Controlled Activity Polymers with Labile Bonds to Pendent Metribuzin in Controlled Release of Bioactive Materials, R. Baker, Academic Press, New York, pages 317-330). However, it was found that metribuzin formed covalent linkages with the polyvinyl alcohols which resulted in hindering its release from the alcoholic polymer for plant uptake. Certain pine craft lignins have shown some decrease in the leaching losses of atrazine and 2,4-D (see Weed Science, E. P. Dunigan and T. Macintosh, 1971, Volume 29 pages 279-282 and Controlled Release Technologies: Methods, Theory and Application by H. T. Dellicolli, 1980, Volume II, C.R.C. Press, Boca Raton, Florida, pages 225-234). Several other leaching inhibitors have been proposed; however, the chemicals currently used to inhibit downward movement have been found to be highly specific to certain chemical types and do not extend generally to plant treating agrichemicals of different chemical classes.

Accordingly, it is an object of this invention to provide a leach inhibiting chemical which is more broadly effective in preventing or inhibiting downward movement of various plant treating materials.

Another object of this invention is to provide an economically produced chemical which prevents or minimizes the movement of toxic chemicals in the soil and retains the plant treating agent in the root or immediate surrounding area of the soil where it is applied and where it is most effective.

Another object of this invention is to provide a leach inhibiting chemical composition which permits more efficient use of a crop treating agent in reduced amounts and which prevents or minimizes contamination of the aquasystem.

These and other objects of the invention will become apparent to one skilled in the art from the following description and disclosure.

THE INVENTION

For effective leaching control, a balance between hydrophilic and hydrophobic moieties in the control agent is required. This balance depends upon the structure and properties of the active component, i.e. the agrichemical and the components in its formulation with additives such as surfactants, certain carriers, emulsifiers, etc. Balance is achieved by means of the present leach controlling agent which is incorporated into the agrichemical formulation by blending, by complexing or by coprecipitating with the active agrichemical. Thus, in accordance with this invention, there is provided a leach inhibiting copolymer having pendant nitrogenous groups which is readily formulated with or incorporated into a plant treating agent; which copolymer having pendant nitrogenous groups contains between about 40 and about 98 wt. % of monomer unit A defined by the formula

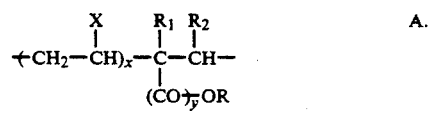

and mixtures of comonomer A and 2 to 40 wt. % of comonomer unit B

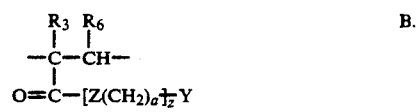

wherein

X is hydrogen, a $C_1$ to $C_{22}$ radical of the group alkyl, alkoxy, aryl, alkaryl, aryloxy and alkaryloxy;

$R_2$ is hydrogen or $-(CO)_{y'}OR'$;

R, $R_1$, $R_3$ and R' are each selected from the group of hydrogen and lower alkyl;

$R_6$ is hydrogen or

x, y, y' and z each have a value of 0 or 1;

a has a value of from 2 to 4;

Z is $-O-$ or $-NH-$

Y is an optionally quaternized group of

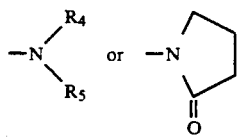

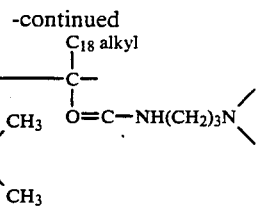

and $R_4$ and $R_5$ are hydrogen or lower alkyl except that at least one of $R_4$ and $R_5$ is lower alkyl and mixtures of comonomer B.

The present copolymers possess superior leach inhibiting properties which is in part due to the quaternized, tertiary or secondary amino groups depending from the linear polymer chain. These pendant groups provide positively charged sites which can act as an anchoring groups for the negatively charged silicate soil surface.

Examples of suitable alpha olefin units (A) include organo methyl vinyl ether, organo acrylate or methacrylate; organo vinyl alcohol; organo maleic acid; organo gutyl maleate; maleic acid ethyl ester; acrylic or methacrylic acid; methyl, methacrylate or acrylate; maleic acid wherein said organo group is preferably $C_2$ to $C_{18}$ alkyl; phenyl optionally substituted with lower alkyl, lower alkoxy or alkenyl; benzyl; phenyloxy optionally substituted with lower alkyl and the like. Illustrative of comonomer B units are

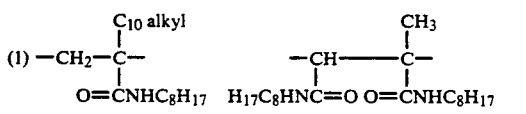

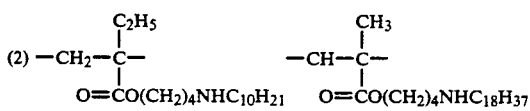

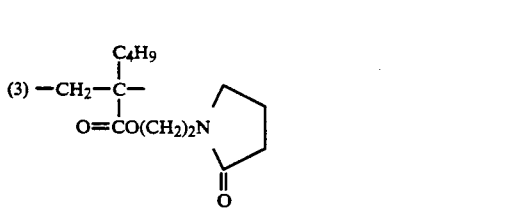

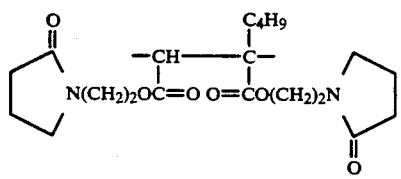

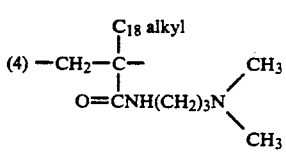

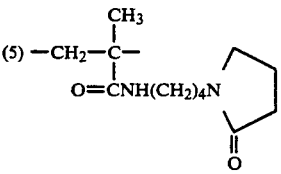

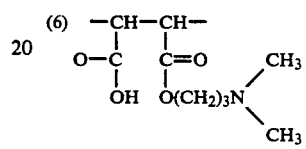

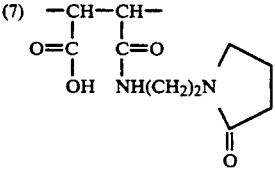

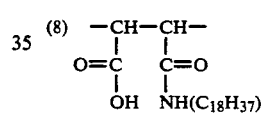

(8)  —CH—CH—
     |    |
   O=C    C=O
     |    |
    OH   NH($C_{18}H_{37}$)

The copolymers of this invention are those having a number average molecular weight greater than 20,000, preferably between about 50,000 and about 150,000. The polymers also having a polydispersity* of from about 4 to about 8, most desirably about 6, are considered the best for providing uniform formulations of high efficiency.

The preferred copolymers of this invention are those shown in following Table A.

TABLE A

| | Polymer | Mn* |
|---|---|---|
| 1. | Methylvinylether/maleic acid polymer having about 60 mole % of the maleic acid units converted to N-[3-(2-oxo-1-pyrrolidonyl) ethyl] amid units | 50,000–100,000 |
| 2. | Methylvinylether/maleic acid having 40 mole % of the maleic acid units converted to N-[3-(2-oxo-1-pyrrolidonyl)ethyl] amide and 20 mole % of the maleic acid units converted to N-octadecyl amide units | 50,000–100,000 |
| 3. | Methyl vinyl ether/maleic acid polymer having about 60 mole % of the maleic acid units converted to N-[3-(N,N-dimethylamino) propyl] amide units | 50,000–100,000 |
| 4. | Methyl vinyl ether/maleic acid polymer having about 10 mole % of | 50,000–100,000 |

TABLE A-continued

| Polymer | Mn* |
|---|---|
| the maleic acid units converted to N-octadecyl-amide units and 50 mole % of maleic acid converted to N-[3-(N,N-dimethylamino) propyl] amide units | |
| 5. AMPHOMER ®** | >20,000 |
| 6. ULTRAHOLD ® 8*** | >20,000 |

*Wt. Av. Molecular weight (Mw)/No. Av. Molecular Weight (Mn)
**AMPHOMER ® is a polymer supplied by National Starch & Chemical Corp., defined as a copolymer of octylacrylamide, t-butylaminoethyl methacrylate and 2 or more monomers of acrylic acid, methacrylic acid or their esters

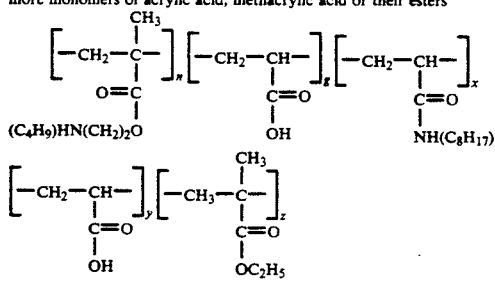

***ULTRAHOLD ® 8 is a polymer supplied by BASF, defined as a terpolymer of acrylic acid, ethyl acrylate and N-t-butyl acrylamide

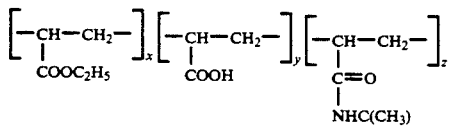

The above polymer/agrichemical composition is applied to the plant or surrounding soil area in a pre-emergent or post-emergent application and in an effective leach inhibiting, plant tolerating amount. In formulation with the active agrichemical, as little as 0.001 weight % of instant polymers, based on the total composition, is effective to inhibit leaching of various agrichemicals. However, a weight ratio of agrichemical to polymer of between about 0.1:1 and about 10:1 is recommended and between about 0.3:1 and about 2:1 is preferred. The resulting agrichemical/leach inhibitor composition is formulated to provide a liquid, preferable of a sprayable consistency, and in some cases may require the addition of an inert diluent.

Representative crop treating agents which are commonly employed and which are controlled by the present leach inhibition agents include a wide range of herbicides, nematocides, insecticides, fungicides, plant growth promoting or regulating chemicals and other crop treating products. These include herbicides such as Dicamba, Alachlor, Aldicarb, Amiben, Arsenal, Assert, Atrazine, Bentazon, Bromacil, Bialaphos, Butylate, Carbofuran, Chloramben, Chlortoluron, Cyanazine, Banval, Cotoran, Dalapon, 2,4-D, Dicamba, Dinoseb, Diquat, Diuron, EDB, EPTC, Glyphosate, Glean, Hyvar, Linuron, Lexone, Lontrel, Monuron, Metribuzin, Mecoprop, Nortron, Norflurazon, Pramitol, Prometryn, Pyramin, Rhizobitoxin, Reflex, Scepter, Simazine, Sinbar, Tordon, Tentoxin, Terbacl, Trifluralin, Urea Derivatives, Velpar, etc.; insecticides such as Azodrin, Diazinon, Dylox, Furadan, Metasystox, Mocap, Phosphamidon, Temik, Trigard, Vydate; Nematocides such as Aldicarb; plant growth regulants such as chloroethylphosphonic acid; fungicides such as Triforine, Penconazole, Bendiocarb and others cited in The Agricultural Handbook, 2nd Ed., Royal Society of Chemistry, (1987). The agrichemicals which are particularly compatible and efficacious with the present leach inhibiting agents include atrazine, dicamba, bromacil, diuron, assert bisulfate, simazine, diazinone, perconazide, triforine and metolachlor.

All of the above agrichemicals are known and appropriate plant dosages and tolerances have been described for each product. Also their agrichemical formulations are well known and such are compatable with the present leach inhibiting agents in the aforementioned concentrations. The formulated active agents can be sprayed or misted to contact treating sites according to known procedures. Since the present lactam nitrogeneous polymers are non-toxic, their incorporation into the formulation does not alter, and in some cases may reduce, the required effective dosage of active agrichemical.

The inhibiting effect of the present polymers is achieved by their complexing, encapsulation, or blending with the agrichemical and applying to a plant site. In the leach inhibiting copolymers of the present invention, the lactam ring provides the hydrophilic moiety and the alkyl chain of the copolymer provides the hydrophobic portion. Correct balance between the hydrophilic and hydrophobic portions enable bonding of the agrichemical to the polymer and also cause a portion of the polymer to bind to the soil surface by either hydrophobic or hydrophilic interaction with organic matter in the soil. Thus, the polymer, together with the agrichemical, is more securely bound to the soil site where it is applied and leaching by rain water is significantly reduced. In all instances, using the above active chemicals, a marked reduction, and in some cases, almost complete elimination of downward transmigration of the agrichemical from the immediate application area through the soil stratum is achieved.

The agrichemical formulations containing the present polymers lactams can be directly prepared by simply mixing the polymer into the standard agrichemical formulation or a preformed agrichemical concentrate thereof followed by recommended dilutions under ambient conditions. With certain agrichemicals, complexing with the polymer provides the highest leaching inhibition, with others, blending with the polymer achieves best results. The soil also has an important role in leaching such that the greatest leachability is found in highly porous, low organic Florida soils; whereas the loamy or clay soils of the midwest or northeast suffer least.

An advantage of the present leach inhibiting compounds is that they are non-specialized with respect to a certain group of agrichemical treating agents since the molecule contains both lipophilic and hydrophilic moieties. Also, the use of the present compounds affords more efficient use of the agrichemical since the later is retained in the immediate surrounding soil area or in the vicinity of the plant root system. Thus, somewhat smaller amounts of the agrichemical are often efficacious. Additionally the present polymers provide control of agrichemical leaching over a prolonged period of time so that less agrichemical need be applied in the next crop application. Another advantage is that the present compounds of lower molecular weight do not alter the dispersion properties of the agrichemical formulation and in some cases may enhance sprayability. In those cases where incorporation of the polymer results in raising the viscosity to an undesirable level, an inert diluent such as a petroleum distillate, mineral oil, water, ethylene glycol, etc. can be added to the formulation. Various surfactants can also be included in the agrichemical formulation. These include anionic sulfonates, e.g. lignin sulfonate, naphthalene/formaldehyde condensate sulfonate, etc. and non-ionic alkoxylated phenols, e.g. ethoxylated or propoxylated nonyl or octyl phenols which can be present in an amount up to about 15 wt. % of the total composition.

Another advantage of the present invention is that the leach inhibiting formulation can also be applied as a powder for crop dusting; in which case the formulation is dried to a particulate solid before use. A further advantage of the present polymers is that they are non-toxic and environmentally safe; thus, they do not add to soil contamination. Additionally, the presence of lactam containing polymers adds to the organic content of the soil, thus benefiting future crops. These and many other advantages will be realized by the use of the present polymeric compounds.

Having thus generally described the invention, reference is now had to the accompanying examples which illustrate specific and preferred embodiments, but which are not to be construed as limiting to the scope of the invention as more broadly described above and in the appended claims.

EXAMPLE I

Preparation of Polymer 1

This experiment was carried out in a 2-liter 4-neck round bottom flask equipped with an overhead stirrer, condenser, thermocouple and dropping funnel. A charge was made to the flask of 312 grams of Gantrez® AN-119* and 900 ml of methyl t-butyl ether. The mixture is stirred and heated to reflux (55° C.) after which a mixture of aminoethyl pyrrolidone (153.6 grams) and 100 ml of methyl t-butyl ether were combined and added over a period of 15-30 minutes by means of the dropping funnel while heating at reflux and stirring for an additional 6 hours.

*poly(methyl vinyl ether/malic anhydride having a specific viscosity of 0.2-0.4 and a molecular weight of 200,000-300,000.

The resultant slurry was filtered to remove the solvent and recover a white solid. The solid was then dried in a vacuum oven at about 45° C. overnight. The anhydride was then converted to the acid form by adding 100 grams of the anhydride slowly to 400 grams of water and stirring at about 70° C. The stirring and heating was continued for about 6 hours after the complete addition of the anhydride. Finally, the 20% aqueous solution of polymer was dried by rotary evaporation at about 70° C. under vacuum followed by vacuum drying the solids in a shallow pan to maximize surface area. The dry powder was then pulverized with a mortar and pestle.

EXAMPLE II

Preparation of Polymer 2

The procedure of the preparation of polymer 1 as described above was followed except that the amount of aminoethyl pyrrolidone used was 102.4 grams and the aminoethyl pyrrolidone was combined with 107.6 grams of octadecyl amine and about 150 ml of methyl t-butyl ether in the dropping funnel before adding it to the slurry of Gantrez® AN-119 as before. Isolation of the anhydride and conversion to the acid form as above were repeated.

EXAMPLE III

Preparation of Polymer 3

A two liter round bottom flask equipped with a condenser, mechanical stirrer, thermocouple with controller, nitrogen inlet tube and dropping funnel is charged with the following:

| | |
|---|---|
| Methyl vinyl ether/maleic anhydride copolymer (MW ~ 75,000) | 312 grams (2.0 moles) |
| Methyl t-Butyl Ether | 700 grams |

The mixture is started stirring and heated to reflux temperature at 55° C. The addition of dimethylaminopropyl amine (122.4 grams; 1.2 moles) dissolved in 300 ml of methyl t-butyl ether is added dropwise over a period of 20 minutes. The reaction is then maintained at 55° C. with agitation for a period of six hours. The resulting mixture is then cooled to room temperature and filtered to recover a white solid which is then dried overnight in a vacuum oven at about 40°-45° C.

This material is then converted to the acid form by hydrolysis. A 100 grams of the above anhydrous material together with 400 grams of distilled water are transferred to a 1-liter glass flask equipped with a thermocouple with controller, overhead stirrer, condenser and nitrogen inlet. The mixture is heated and stirred at about 70° C. for 6 hours. The resulting solution is then dried partially by rotary evaporation. Some hydrogen peroxide, up to 3 ml/100 ml of solution, may be added in order to preserve a white color. The drying is completed by pouring the viscous partially dried material into a shallow pyrex dish and drying overnight in a vacuum oven at about 45° C. and polymer 3 is recovered as particulate product.

EXAMPLE IV

Preparation of Polymer 4

Polymer 4 is prepared by the same general method as described for Polymer 3 except that the dimethylaminopropyl amine is introduced along with 0.2 moles of octadecyl amine in 300 ml of methyl t-butyl ether.

The preparation of the acid form follows the same general outline previously described in Example III, except that a 10% solution is prepared by using 1000 ml of water. The resulting product does not go into solution but remains in suspension. The suspension is dried as before with a preliminary drying by rotary evaporation followed by more complete drying in a vacuum oven and the white solid which is Polymer 4 is recovered and ground into powder.

EXAMPLES V-X

The polymers 1 and 2 were mixed with agrichemicals A-C.

AGRICHEMICALS
A. Dicamba
B. Atrazine
C. Metolachlor

The above agrichemicals possess widely disparate chemical properties as shown in Table B.

TABLE B
CHEMICAL PROPERTIES OF HERBICIDES

| Herbicide | Chemical Nature | Solubility (mg/L) | Half Life (d) | $K_{oc}$ | Leaching Potential+ |
|---|---|---|---|---|---|
| Atrazine | Basic | 33 | 60 | 100 | 17 |
| Dicamba | Acidic | 400,00-0* | 14 | 2 | 1.4 |
| Metolachlor | Nonionic | 530 | 90 | 200 | 22 |

+Leaching Potential is $K_{oc}$/half life × 10. The leaching potential varies inversely with the number value
*as dimethyl ammonium salt The following mixing procedures X-Z were employed to prepare the polymer/agrichemical compositions.

X. The agrichemical (15 g.) and the polymer (15 g.) were dissolved in a common solvent and mixed at 55° C. for 4 hours; after which the solvent used for solubilizing was stripped off under reduced pressure and the solid polymer/agrichemical product (20–30 g.) was dried and recovered.

Y. The same as procedure X, except that, where the product is an amorphous gel, it was dissolved in a solvent and the final product is a liquid.

Z. The polymer was dispersed in a 10–15% solution of the agrichemical in ethanol (ETOH), tetrahydrofuran (THF) or a mixture thereof and the resulting dispersion or gel was heated to 45±5° C. for 4 hours with agitation. The solvent mixture was then stripped off under vacuum and the product recovered.

The coprecipitated or complexed products of the above Polymers 1 and 2 are reported in following Table I.

TABLE III

| Example | Sample of Ex. | % Agrichem in Effluent | | | | Total |
|---|---|---|---|---|---|---|
| | | First Pore V. | Second Pore V. | Third Pore V. | Fourth Pore V. | |
| XI | IX | 2.6 | 24.9 | 12.0 | 7.9 | 47.4 |
| XII | V | 5.6 | 37.0 | 30.0 | 7.4 | 80 |
| XIII | VII | 6.0 | 28.1 | 23.7 | 9.3 | 67.1 |

The above data shows that by the fourth wash only a minimal amount of the agrichemical was leached out of the immediate vicinity (to a 8 cm depth) of the soil application site.

EXAMPLES XIV-XIX

Blends of the above polymer/agrichemicals in commercial formulations containing surfactant, emulsifier and diluent were prepared as follows.

The polymer (5.0 g on 100% basis) was added to each of the following commercial agrichemical liquid formulations D–F to provide a weight ratio of 1:1 polymer to agrichemical and diluted with water to obtain a solution containing 10 wt. % of polymer and 10 wt. % of agrichemical.

D. Banvel herbicide containing 40% Dicamba in 4 lbs/gal of water

E. Aatrex 4L containing 40.8% Atrazine

F. Dual containing 86.4% Metolachlor to provide a 28.6% solution for D, a 29.0% solution for E and a 46.4% solution for F.

The resulting solutions were then targeted with 8500 cpm of radioactive $^{14}C$ agrichemical of the same species. The resulting mixtures were individually added to the top of a separate column similar to that above at a

TABLE I

| Example No. | Agri-chemical | Polymer | Initial Agri-chemical wt. ratio | Prep. Method | Initial Solubilizing Agent | State of Final Product/Solvent | Assay* |
|---|---|---|---|---|---|---|---|
| V | A | 1 | 1:1 | X | EtOH/H$_2$O | solid/none | 48.9 |
| VI | A | 2 | 1:1 | X | EtOH/H$_2$O | solid/none | 48.0 |
| VII | B | 1 | 1:1 | Z | THF/H$_2$O | solid/none | 53.3 |
| VIII | B | 2 | 1:1 | Z | THF/H$_2$O | solid/none | 51.0 |
| IX | C | 1 | 1:1 | X | EtOH/H$_2$O | solid/none | 54.2 |
| X | C | 2 | 1:1 | Y | EtOH/H$_2$O | liquid/none | 10.3 |

*by UV analysis,
% Agrichemical

EXAMPLES XI-XIII

The above polymer/agrichemicals were each targeted with 8500 cpm* of the corresponding radioactive $^{14}C$ doctored agrichemical and then introduced at a rate of 5 lbs/acre into the top of an open bottom plexiglass 7 cm diameter, 8 cm long column containing 450 g of Polk County Florida surface soil. Then, water at room temperature was added in 4 increments of 125 ml. each to simulate 4 pore volumes i.e. normal rain conditions. The $^{14}C$ activity in each of the effluent solutions was assayed and the relative % of agrichemical recovered compared to 100% recovery in the absence of the present polymer is reported in the following Table II.
* curie/million rate of 5 lbs. agrichemical/acre and the leachates from each of the 4 water washings were collected and analyzed.

The column employed in this study was used at bulk density of soil at packing. Each pore volume of water applied on the top of the soil column was equivalent to 3.2 cm (1.28 inch) of rainfall. The amount of herbicide leached was calculated on the basis of $^{14}C$-herbicide applied and recovered from the leachate. The difference between these two values represented that which was adsorbed by the soil.

Controls were run under exactly the same conditions with the same agrichemicals, except that the inhibiting polymer of this invention was omitted. In each control 100% leaching of agrichemical occurred. The analysis of the leachate from each of the 4 pore volumes is reported in following Table III.

TABLE III

| | | | Relative % of Agrichemical Recovered Compared To 100% Leaching with Control* | | | | |
|---|---|---|---|---|---|---|---|
| Example | Polymer | Agrichemical | 1st Pore | 2nd Pore | 3rd Pore | 4th Pore | Total |
| XIV | 1 | D | 32.9 | 45.1 | 7.2 | 3.5 | 88.7 |
| XV | 2 | D | 31.8 | 36.1 | 3.0 | 3.1 | 74.0 |
| XVI | 1 | E | 5.9 | 37.0 | 24.0 | 20.5 | 87.6 |
| XVII | 2 | E | 6.7 | 38.0 | 28.9 | 15.9 | 89.5 |
| XVIII | 1 | F | 20.3 | 39.0 | 27.6 | 5.1 | 92.0 |
| XIX | 2 | F | 20.9 | 32.7 | 10.0 | 11.3 | 74.9 |

*By $^{14}C$ activity assay using Scintillation counter, % Agrichemical

EXAMPLES XX-XXV

Bioassays of selected samples (i.e. products of Examples XIV-XVII) were made and results reported in Table IV. The procedure for these examples is as follows.

The indicated polymer/agrichemical formulation was introduced into a 130 cm × 10 cm soil packed column. In these experiments, 2.5 cm simulated rainfall was used for Dicamba 7.5 cm simulated rainfall for Atrazine and Metolachlor was employed by adding water at the rate of 1.5 cm/hr. After leaching, the columns were allowed to drain overnight and split longitudinally into two halves. Each half was planted with alfalfa or rye grass (as indicated) in 5 cm spaced rows. The % injury as a function of herbicide movement at different heights are shown in Table IV.

At every 15 cm from bottom of the column, a ridge of silicone was applied on the inside wall of each half of the column to prevent "edge flow" of water along the soil-wall interface. A PVC end-cap with a small drain hole was fitted to the bottom of the column and the columns were packed with Florida soil from respective depths to provide a Florida soil profile. Soil-packed columns were kept in upright position and the soil was saturated with water and allowed to drain overnight; after which the commercial formulation of herbicide (5 kg ai/ha) with or without polymers (5 kg/ha) was introduced to the top of the column. A 2 ml solution of each treatment was applied uniformly on the soil surface as several drops using pasteur pipet. Columns were leached by pouring distilled water over filter paper placed on the soil surface to ensure uniform distribution of water and leaching was measured at 15, 30, 45, 60 and 60+ cm depths.

TABLE IV

| % Alfalfa Injury (Application rate 5 kg/ha or 4.5 lbs/acre) | | | | | | |
|---|---|---|---|---|---|---|
| | | Column Depth (cm) | | | | |
| Example | Sample % of Ex. | 0–15 | 15–30 | 30–45 | 45–60 | 60–120 | Total % Decrease |
| XX | XIV | 100 | 100 | 100 | 42 | 0 | 14 |
| XXI | XV | 100 | 100 | 100 | 84 | 0 | 4 |
| XXII | XVI | 100 | 50 | 0 | 0 | 0 | 25 |
| XIII | XVII | 100 | 50 | 0 | 0 | 0 | 25 |

Controls with no polymer gave 100% injury at all depths from 0–60 cm for Dicamba (D) and 0–30 cm for Atrazine (E) formulations

| % Rye Grass Injury (Application rate 10 kg/ha or 8.9 lbs/acre) | | | | | |
|---|---|---|---|---|---|
| | Sample % | Column Depth (cm) | | | Total % |
| Example | of Ex. | 0–15 | 15–30 | 30–120 | Decrease |
| XXIV | XVIII | 100 | 66 | 0 | 17 |
| XXV | XIX | 100 | 50 | 0 | 25 |

Controls with no polymer gave 100% injury at all levels 0–30 cm for metolachlor (F) formulations.

The above examples illustrate various embodiments and preferred leach inhibiting compositions of this invention; however, it will be understood that substitutions of the crop treating chemicals referred to in the foregoing description, or their mixtures, can be made to replace those used in the respective Examples without departing from the scope of this invention. Similarly, any of the polymers set forth in the foregoing disclosure, or their mixtures, can be substituted for those employed in the above Examples, to provide leach inhibition of the agrichemical selected. From the above description, it will also become apparent that many modifications and alterations can be made in the preparations of the leach inhibiting compositions which are within the scope of this invention.

What is claimed is:

1. A leach inhibiting agrichemical composition comprising an active plant growth regulating agrichemical, an inactive carrier and a leach inhibiting amount of a polymer having pendent nitrogenous groups which polymer contains between about 40 and about 98 wt. % of monomer unit A defined by the formula

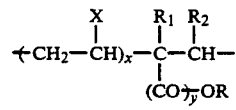

and mixtures of said monomers and 2 to 40 wt. % of comonomer unit B

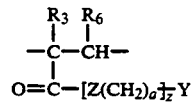

wherein X is hydrogen, a $C_1$ to $C_{22}$ radical of the group alkyl, alkoxy, aryl, alkaryl, aryloxy and alkaryloxy;

$R_2$ is hydrogen or —$(CO)_{y'}OR'$;

R, $R_1$, and $R_3$ are each selected from the group of hydrogen and lower alkyl;

$R_6$ is hydrogen or

x, y, y' and z each have a value of 0 or 1;
a has a value of from 2 to 4;
Z is —O— or —NH—
Y is an optionally quaternized group of

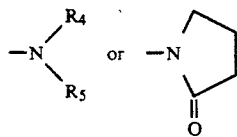

and

R₄ and R₅ are hydrogen or alkyl except that at least one of R₄ and R₅ is alkyl; said copolymer having a number average molecular weight greater than 20,000.

2. The composition of claim 1 wherein the copolymer contains between about 10 and about 40 wt. % of comonomer B.

3. The composition of claim 1 wherein the weight ratio of agrichemical to polymer is between about 0.1:1 and about 10:1.

4. The composition of claim 3 wherein said ratio is between about 0.3:1 and about 2:1.

5. The composition of claim 1 wherein the polymer is the polymer of maleic acid, a $C_1$ to $C_4$ alkyl vinyl ether and a comonomer wherein Z is —NH—, z is one, a is two and Y is a pyrrolidonyl radical.

6. The composition of claim 1 wherein the polymer is the polymer of a $C_1$ to $C_4$ alkyl ester of maleic acid, a $C_1$ to $C_4$ vinyl ether and a comonomer mixture of one comonomer wherein z is zero and Y is octadecylamine and another comonomer wherein Z is —NH—, z is one, a is two and Y is a pyrrolidonyl radical.

7. The composition of claim 6 wherein the vinyl ether is methyl vinyl ether.

8. The composition of claim 1 wherein the polymer is the polymer of maleic acid, a $C_1$ to $C_4$ alkyl vinyl ether and a comonomer wherein Z is —NH—, z is one a is three, and Y is —N(CH₃)₂.

9. The composition of claim 8 wherein said ether is methyl vinyl ether.

10. The composition of claim 1 wherein the polymer is the polymer of maleic acid, a $C_1$ to $C_4$ alkyl vinyl ether and a comonomer mixture of one monomer where Z is —NH—, z is one, a is 3, and Y is —N(CH₃)₂ and another comonomer wherein z is zero and Y is octadecylamine.

11. The composition of claim 10 wherein said ether is methyl vinyl ether.

12. The composition of claim 10 wherein said ether is butyl vinyl ether.

13. The composition of claim 1 wherein said carrier is an aqueous solution.

14. The composition of claim 10 wherein said carrier is water.

15. The composition of claim 10 wherein said carrier is an aqueous alcohol solution.

16. The composition of claim 1 wherein the number average molecular weight of the polymer is between about 50,000 and about 150,000.

17. A method of inhibiting leaching of an active plant growth regulating agrichemical which comprises contacting a plant or plant site with a leach inhibiting amount of the composition of claim 1.

18. The method of claim 17 wherein said composition is applied in a dry state.

19. The method of claim 17 wherein said composition is applied in an aqueous solution.

* * * * *